United States Patent [19]

Petereit et al.

[11] Patent Number: 5,133,970
[45] Date of Patent: Jul. 28, 1992

[54] WATER-SOLUBLE PRESSURE-SENSITIVE SKIN-ADHESIVE AND USE THEREOF

[75] Inventors: Hans-Ulrich Petereit; Erna Roth, both of Darmstadt, Fed. Rep. of Germany

[73] Assignee: Röhm GmbH Chemische Fabrik, Darmstadt, Fed. Rep. of Germany

[21] Appl. No.: 550,991

[22] Filed: Jul. 11, 1990

[30] Foreign Application Priority Data

Jul. 24, 1989 [DE] Fed. Rep. of Germany ....... 3924393

[51] Int. Cl.$^5$ ............................................. A61F 13/00
[52] U.S. Cl. .................................. 424/443; 424/448; 424/449; 428/413; 526/313
[58] Field of Search ....................... 424/448, 449, 443; 524/522; 523/406; 264/184; 428/413; 526/312

[56] References Cited

U.S. PATENT DOCUMENTS

| | | | |
|---|---|---|---|
| 3,321,451 | 5/1967 | Gander et al. | 260/793 |
| 3,598,123 | 8/1971 | Zafferend | 428/268 |
| 4,078,568 | 3/1978 | Etes | 128/283 |
| 4,138,446 | 2/1979 | Kawakami | 526/312 |
| 4,514,551 | 4/1985 | Furuno | 526/312 |
| 4,588,757 | 5/1986 | Minnis | 523/406 |
| 4,705,695 | 11/1987 | Lehmann et al. | 427/3 |

FOREIGN PATENT DOCUMENTS 0164669 12/1985 European Pat. Off. .
1523183 3/1968 France .

OTHER PUBLICATIONS

Isono et al., Chem. Abstracts, vol. 85, Abstract No. 92226t (1976).
*Pharmaceuticals,* (1976), vol. 85, 99226t, "High--Molecular-Weight Bandage Composition" Isono et al.

*Primary Examiner*—Thurman K. Page
*Assistant Examiner*—D. Gabrielle Phelan
*Attorney, Agent, or Firm*—Oblon, Spivak, McClelland, Maier & Neustadt

[57] ABSTRACT

A water-soluble salt of a copolymer containing a monoethylenically unsaturated monomer containing amino groups that can be radically polymerized and at least one alkyl ester of acrylic and/or methacrylic acid, is used as a flexible pressure-sensitive adhesive for application to the skin.

20 Claims, No Drawings

WATER-SOLUBLE PRESSURE-SENSITIVE SKIN-ADHESIVE AND USE THEREOF

BACKGROUND OF THE INVENTION

1. Field of the Invention

This invention relates to a pressure-sensitive skin adhesive for fastening flat, flexible substrates such as bandages, wound plasters, and adhesive plasters or transdermal drugs to the skin. The invention also relates to a solution of the pressure- sensitive skin adhesive and its use for coating on flexible, flat substrates. Finally, the invention also relates to wound plasters, adhesive plasters and transdermal drugs.

2. Discussion of the Background

In accordance with JP-A 76/75 745 (Chem. Abstr. 85, 99226), for fastening bandages to the skin of a patient, a copolymer of a dialkylaminoalkyl methacrylate and an alkyl methacrylate that is not adhesive by itself is used in combination with a sufficient amount of a plasticizer such as polypropylene glycol or tributyl citrate. The adhesive is not water-soluble. The same applies to a pressure-sensitive skin adhesive pursuant to FR 1,523,183, which contains a crosslinked copolymer of dimethylaminoethyl methacrylate and an alkyl acrylate in the form of an aqueous dispersion.

U.S. Pat. No. 3,321,183 discloses a pressure-sensitive skin adhesive that contains a salt of a copolymer of an ethylenically unsaturated monomer containing an amino group that can be polymerized by a radical mechanism, and at least one alkyl ester of acrylic acid. The skin adhesive is not water-soluble to a clear solution and is therefore used in the form of a solution in alcohol, acetone, or a mixture of these with water, but can be washed off of the skin with water. Salt-forming acids mentioned are hydrochloric acid, organic sulfonic acids and carboxylic acids, such as acetic acid, propionic acid, and benzoic acid.

EP-A 164 669 describes a coating agent for pharmaceutical dosage forms that contains an acrylic and/or methacrylic polymer with tertiary ammonium groups in the side chain in aqueous solution. The coating agent solution dries to hard, nonadhesive coatings.

SUMMARY OF THE INVENTION

Accordingly, one object of the present invention is to overcome the deficiencies of these prior art adhesives and to provide a pressure-sensitive, permanently flexible or elastic skin adhesive that can be applied without using organic solvents and can be removed from the skin with water.

This and other objects which will become apparent from the following specification have been achieved by the present flexible pressure sensitive adhesive which contains an uncrosslinked copolymer salt. The copolymer salt contains monomer units corresponding to an amino group-containing monoethylenically unsaturated monomer and at least one alkyl ester of acrylic acid, methylacrylic acid or a mixture thereof. A sufficient number of the amino groups of the amino group-containing monomers are present in the salt form to render the copolymer salt soluble in water. The flexible adhesive can be applied directly to the skin to adhere objects to the skin or can be fabricated as an adhesive film on medical plasters and devices for the transdermal application of pharmaceutical compounds to adhere the plaster or device to skin.

DETAILED DESCRIPTION OF THE PREFERRED EMBODIMENTS

The term "pressure-sensitive adhesive" means that it is permanently flexible or elastic as a dried film and is removably attached when pressed onto a solid substrate. However, the dried adhesive film does not have to be anhydrous. The desired adhesiveness frequently occurs only when the adhesive film is dried out in the air and does not dry further by itself, but is in moisture equilibrium with the skin.

The pressure-sensitive skin adhesive of the present invention contains a salt of an uncrosslinked copolymer of a monoethylenically unsaturated monomer containing amino groups that can be polymerized by a radical mechanism, and at least one alkyl ester of acrylic acid and/or methacrylic acid that is water-soluble in the salt form. The solubility in water is provided by a sufficiently high proportion of the monomer containing amino groups in the salt form. The more hydrophobic the acrylic ester used as comonomer is, i.e., the longer its alkyl group is, the larger the amino-containing monomer salt proportion must be. Typically, about 50–100%, preferably about 80–100% of the amino groups are in the salt form.

The copolymer is considered to be "water-soluble" in the context of the present invention when it produces at least a 1 percent clear and homogeneous solution in pure water at 20° C. in which the copolymer is present in molecularly disperse form.

The permanently flexible or elastic properties that are the prerequisite for pressure sensitivity are achieved in a moisture-containing film by a suitable choice of the monomer components of the copolymer or by the addition of organic plasticizers or by a combination of these measures.

The preferred skin adhesives of the present invention contain 2–200 wt % (based on the copolymer) of an organic plasticizer. In addition, agents which increase the hydrophilic properties, such as glycerin, urea or sorbitol, may be added to the adhesives. The hydrophilic agents themselves have only limited inherent plasticizing action, but serve to prevent or hinder evaporation of water from the adhesive film and thereby promote retention of plasticity, elasticity and flexibility over an extended period by means of the retention of moisture. Such hydrophilic agents can be employed in amounts from about 10 wt % to several hundred wt %, i.e. about 200–400 wt % (based on the copolymer).

Water has a plasticizing action on the copolymers used pursuant to the present invention. This action usually becomes effective when the adhesive is applied to the skin since the pressure-sensitive adhesive film is in moisture equilibrium with the skin. When producing pressure-sensitive adhesive films on substrates, it is not desirable for the same reason to dry the film beyond this equilibrium value. The desired adhesiveness usually occurs with a moisture content of about 1 to 10 wt. % based on the anhydrous copolymer.

The pressure-sensitive skin adhesive is considered to have pressure-sensitive adhesion in the context of the present invention when it shows an adhesive force of at least 1 N/cm (peel method) in the adhesion test according to European Pharmacopoeia, Second Edition, Part II-7, pp. 273 ff (1984).

It is known that the higher alkyl esters of acrylic and/or methacrylic acid impart softness and adhesiveness to copolymers prepared from them. At the same time, they make the copolymer hydrophobic and water-insoluble. In determining the proportion of the ethylenically unsaturated monomer containing amino groups that should be polymerized, one should consider that the proportion of these monomers must be large enough on the one hand to provide solubility in water, and small enough on the other hand to enable copolymerization of an adequate proportion of the plasticizing alkyl acrylate or methacrylate. When the monomers used to make up the copolymer do not allow these two properties to be achieved at the same time at any ratio, an additional plasticizer can be added for assistance.

However, the adhesiveness of the copolymer depends not only on its content of alkyl acrylate or methacrylate monomers, but also on the type of monomer containing the amino groups. An alkylene chain up to a limit of about 10 carbon atoms, may be present in the amino group-containing monomer as a spacer group between the unsaturated polymerizable group and the amino group, and promotes the softness of the copolymer. Alkylene groups above this limit reduce the mobility of the polymer chain to which they are bound, and thereby increase its hardness.

The anion ($X^-$) of the acid as whose salt the copolymer is present exerts a strong effect on softness. While the anions of inorganic acids and of the lower organic sulfonic acids and carboxylic acids promote the hardness of the copolymer, it has been found surprisingly that the anions of higher carboxylic acids have a plasticizing effect. Suitable carboxylic acids contain at least 4 and preferably 8 to 20 carbon atoms. Preferred carboxylic acids of this group are capric acid, lauric acid, and myristic acid. If the necessary water solubility is not achieved with these higher carboxylic acids a mixture of higher and medium-chain ($C_{2-8}$) carboxylic acids or dicarboxylic acids, such as adipic acid, can be used. The proportion of medium-chain carboxylic acids can amount to as much as 30 mole-% of the anionic equivalents, for example.

The proportion of the monomers containing amino groups in the copolymer is preferably about 30 to 80 wt. %. It is preferred that the monomers be esters or amides of acrylic and/or an alkylacrylic acid that have the following structures

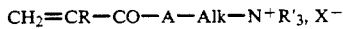
$$CH_2=CR-CO-A-Alk-N^+R'_3, X^-$$

or

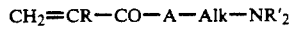
$$CH_2=CR-CO-A-Alk-NR'_2$$

in which R is a hydrogen atom or a $C_{1-4}$ alkyl group, preferably methyl, A is an oxygen atom or an amino group, preferably —NH—, Alk is a straight chain or branched alkylene group, preferably with 2 to 8 carbon atoms, R' is identical or different organic groups with up to 22 carbon atoms, particularly alkyl, aryl, or aralkyl groups, where a maximum of two of the R' groups are hydrogen atoms. $X^-2$ represents the acid anion for which examples have already been given above.

Preferred alkyl groups for R' contain 1–6 carbon atoms, i.e., methyl, ethyl, propyl, isopropyl, n-butyl, isobutyl, sec-butyl, pentyl and hexyl. Two of the R' groups together with the nitrogen atom to which they are attached may form a nitrogen-containing heterocyclic ring. Preferred heterocyclic rings are rings having 5–8 atoms in the ring, preferably 5–6 atoms in the ring. The heterocyclic groups may also contain an additional nitrogen or oxygen atom as one member of the ring.

Typical heterocyclic groups include morpholino and piperidino groups. Preferred aryl groups are phenyl and phenyl substituted with $C_{1-6}$ alkyl groups. Preferred aralkyl groups are alkylphenyl groups containing 7–14 carbon atoms and alkylphenyl groups substituted on the aromatic ring with the $C_{1-6}$ alkyl groups, e.g., benzyl and benzyl substituted on the aromatic ring with $C_{1-6}$ alkyl groups.

Suitable monomers containing amino groups with a tertiary amino group are
Dimethylaminoethyl acrylate and methacrylate,
Diethylaminoethyl acrylate and methacrylate,
Dibutylaminoethyl acrylate and methacrylate,
Morpholinoethyl acrylate and methacrylate,
Piperidinoethyl acrylate and methacrylate,
Dimethylamino-2-propyl acrylate and methacrylate,
Dimethylaminoneopentyl acrylate and methacrylate,
Dimethylaminoethyl acrylamide and methacrylamide,
Diethylaminoethyl acrylamide and methacrylamide,
Dibutylaminoethyl acrylamide and methacrylamide,
Morpholinoethyl acrylamide and methacrylamide,
Piperidinoethyl acrylamide and methacrylamide,
Dimethylamino-2-propyl acrylamide and methacrylamide,
Dimethylaminoneopentyl acrylamide and methacrylamide.

Monomers with several amino groups, such as derivatives of polyethylenimine, are also suitable. Monomers that contain one or more quaternary ammonium groups are also suitable.

Among these are
N,N-Dimethyl-N-(2-methacryloyloxyethyl)aminoacetic acid betaine,
N,N-Dimethyl-N-(2-methacryloylaminopropyl)aminoacetic acid betaine,
Acryloxy- and methacryloxyethyltrimethylammonium chloride,
Acryloxy- and methacryloxyethyltrimethylammonium methosulfate, and
Acrylamido- and methacrylamidoethyltrimethylammonium chloride.

Since quaternary ammonium compounds with carboxylic acid anions are difficult to obtain, it is difficult when using the last-mentioned monomers to make use of the plasticizing action of higher carboxylic acid anions.

Preferred alkyl ester monomers of acrylic acid and/or methacrylic acid, are those with 4 to 14 carbon atoms in the alkyl group, especially the esters of acrylic acid. In particular, n-butyl, n-hexyl, n-octyl, 2-ethylhexyl, n-decyl, and n-dodecyl acrylate are very suitable. The lower esters of acrylic and/or methacrylic acid are usually used only as comonomers along with the higher esters. These lower esters may be present, however, in combined amounts up to about 60 wt %, so long as sufficient long chain alkyl ester monomers are incorporated. Perferably, the lower esters are present in amounts of 0–50 wt %, more preferably 10–35 wt %.

In addition to these, other comonomers can be present in the structure of the copolymer, if they do not reduce the water solubility or increase the hardness beyond allowable limits. Examples are acrylamide and/or methacrylamide, hydroxyalkyl esters and polyalkylene glycol esters of acrylic and/or methacrylic acid, ethylene, vinyl acetate, vinyl propionate, and vinylpyrrolidone. It is not usually necessary to use these monomers to prepare useful pressure-sensitive skin adhesives and their proportion is ordinarily below 20 wt. %.

The copolymer can be produced in aqueous solution in the salt form by radical copolymerization of the neutralized amino monomers with the other monomeric constituents. However, it is preferred first to prepare the unneutralized copolymer by using the monomers in the base form instead of the monomer with an ammonium salt group. Various, known polymerization procedures are available for the radical polymerization of these monomer mixtures, for example polymerization in water or in organic solvents, polymerization in bulk, and since the copolymers are sparingly soluble in the base form, emulsion polymerization in the aqueous phase, and also by "inverse bead polymerization in the organic phase". The organic polymer solutions and aqueous polymer dispersions can be converted into powdered products, for example by spray-drying. The bulk polymers are melted in an extruder and extruded to a fine granulate.

The molecular weight of the copolymer affects the viscosity of the aqueous solution of the pressure-sensitive skin adhesive as a function of concentration, based on the liquid constituent. The molecular weight is preferably in the range between 20,000 and 250,000. The viscosity of the aqueous solution of the copolymer can be adapted to the later application by choice of a suitable concentration. It should generally be no more than 100 Pa.s, preferably about 10 mPa s to 10 Pa.s. The polymer content of the solution is preferably in about the range of 10 to 80 wt. %.

The aqueous solution can be made by stirring the finely divided copolymer in the base form in an aqueous solution of the acid, whereupon it dissolves with the formation of a salt. The dissolution can be hastened by gentle heating. Plasticizers and other additives can optionally be mixed with the final solution. Suitable plasticizers are liquid organic compounds with at least limited water solubility that are compatible with the polymer and are nonvolatile or not substantially volatile under the conditions of processing and use. They should also be non-toxic, and should preferably not migrate into the skin or the applied substrate. There is adequate compatibility when a homogeneous solution can be prepared from the copolymer and the plasticizer, and a clear film can be prepared from this by drying, or when the copolymer can be dissolved in an excess of the plasticizer. Compounds suitable as plasticizers generally have a molecular weight between 200 and 20,000 and contain one or more hydrophilic groups in the molecule, for example hydroxy, ether or amino groups. Examples of suitable plasticizers are triethyl citrate or tributyl citrate, glycerin triacetate, and Polyethylene Glycols 500 to 20,000.

Because of its nontoxic and nonirritating properties, the aqueous pressure-sensitive skin adhesive solution can be applied directly to the skin to form an adhesive surface. After brief drying, the adhesive film can be used to fasten objects such as bandages, clothing, e.g., support stockings and bodices, etc., to skin by pressing lightly on the object having the adhesive interposed between the skin and the object. After the intended time of action, the cemented substrate can be taken off easily, which can also optionally be facilitated by moistening with water. No irritation is observed even when the same areas of skin are coated repeatedly. Because of the hydrophilic nature of the adhesive film, the skin is clearly less affected than when conventional rubber adhesive films are used. The adhesive film remaining on the skin including adhering dirt, fabric fibers, etc., can be washed off easily and quickly with hot or cold water.

The aqueous pressure-sensitive skin adhesive solution is suitable in the same way for producing pressure-sensitive adhesive films on substrates or objects to be adhered to the skin, such as wound plasters, medical adhesive plasters, and adhesive tapes, or on drug devices suitable for transdermal use intended for application to the skin, which have pressure-sensitive skin adhesion. These objects may contain a conventional topical or systemic pharmaceutical ingredient, which can be contained in the adhesive film itself or in the substrate coated with the adhesive film. The substrate may be only partially coated with the adhesive, so long as adhesion to skin is possible. Coating on at least one surface is required. The dried adhesive film, which still contains an adequate amount of moisture, is preferably protected with a conventional release film until it is used and applied to skin.

To produce the adhesive film, a film of the aqueous pressure sensitive skin adhesive solution about 0.01 to 1 mm thick is applied to the substrate or object, and dried for from about 1 min to 24 hours at about 20° to 100 C., for example, with the moisture content not being allowed to drop below that necessary to maintain the desired adhesiveness. If desired, the coating can be repeated several times to reach a greater thickness. Flexible, flat substrates are useful for coating, for example the familiar fabrics, nonwoven fabrics, or films conventional for adhesive plasters. In the same way, special polymer films which act as drug reservoirs, for example, as well as their laminates with metal foils, can be provided with an adhesive film. In the industrial application of the pressure-sensitive skin adhesive pursuant to the invention, it is advantageous that no environmentally polluting or explosive solvent vapors from the drying area require disposal, and that the coating system can be cleaned with just water.

Other features of the invention will become apparent in the course of the following examples which are given for illustration of the invention and are not intended to be limiting thereof.

EXAMPLES

In Examples 1 to 4, a copolymer containing 25 wt. % methyl methacrylate, 26 wt. % n-butyl methacrylate, and 49 wt. % dimethylaminoethyl methacrylate was used.

EXAMPLE 1

135.2 g of the copolymer described above was dissolved in 686.7 g of water, after adding 15.9 g of adipic acid and 78.3 g of lauric acid, by stirring for about 1 hour at about 90° C. After cooling, 82.6 g of glycerin and 1.4 g of sorbic acid were added. The solution was viscous and contained 31.3% dry solids. It could be applied to a skin-colored PVC film (85 microns thick) by doctor blade application on a continuous coating machine with a running speed of 0.5 m/min, and could be dried within 8 minutes with an air feed temperature of 80° C. The amount of adhesive was 0.4 mg/cm$^2$ and reached an adhesive force of 2.5 N/cm. The adhesive film was protected by a PVC film. Plaster bandages cut out of such tapes adhered to the skin for several days and caused no irritation.

EXAMPLE 2

113 g of the copolymer described above was dissolved in 720 g of water, after adding 13 g of adipic acid and 54 g of lauric acid, by heating at 90° C. with stirring for about 1 hour. After cooling, 100 g of glycerin was added.

This solution was clear and contained 28% dry solids. It had a viscosity of 750 mPas and dried on the skin to form adhesive films with an adhesive force of about 1.3 N/cm, which fastened bandages and support stockings securely. After removing the films, residues of adhesive could be washed off of the skin easily with water.

EXAMPLE 3

118 g of the copolymer described above was dissolved in 800 g of water with 14 g of adipic acid and 68 g of lauric acid by stirring and heating for about 1 hour. The clear solution with a dry content of 20% had a low viscosity. It could be coated on aluminum foil and after drying, reached an adhesive force of about 5.7N/cm.

EXAMPLE 4

175 g of the copolymer described above was dissolved in 649 g of water with 19 g of glutaric acid and 84 g of lauric acid by stirring and heating. After cooling, 73 g of glycerin was added. This solution had 35.1% dry solids. After doctor blade application to aluminum foil, the film dried to films with adhesive force of about 4.9N/cm.

EXAMPLE 5

200 g of an aqueous dispersion with a content of 30 wt. % of a polymer consisting of 35 parts ethyl acrylate, 25 parts methyl methacrylate, 30 parts 3-dimethylamino-2,2-dimethylpropyl methacrylate, and 10 parts of a mixture of $C_{12}$- and $C_{14}$-alkyl methacrylate was heated to 60° C. and mixed with 33.2 g of a 10% aqueous solution of adipic acid. It was then heated to 90° C., 16.3 g of lauric acid was added, and the mixture was stirred at this temperature for 2 hours. The cooled solution had a low viscosity and contained 31.9% dry solids. After evaporation of the solvent, it formed adhesive films.

Obviously, numerous modifications and variations of the present invention are possible in light of the above teachings. It is therefore to be understood that within the scope of the appended claims, the invention may be practiced otherwise than as specifically described herein.

We claim:

1. A flexible water-soluble pressure sensitive adhesive, comprising an uncrosslinked copolymer salt, said copolymer containing
   (i) 30 to 80 wt % of monomer units corresponding to an amino group-containing monoethylenically unsaturated monomer and
   (ii) monomer units corresponding to at least one $C_{4-14}$ alkyl ester of acrylic acid, methacrylic acid or a mixture thereof, wherein a sufficient amount of said amino group-containing monomer is in the salt form such that said copolymer salt is soluble in water, said salt comprising higher carboxylic acid anions have 8 to 20 carbon atoms or a mixture of said higher carboxylic acid anions and up to 30 mol percent medium-chain carboxylic acid anions having 2 to 8 carbon atoms or dicarboxylic acid anions.

2. The adhesive of claim 1, wherein said salt form of said amino group-containing monomer has the structure $$CH_2=CR-CO-A-Alk-N^{\oplus}R'_3 X^{\ominus}$$

wherein R is hydrogen or a $C_{1-4}$ alkyl group, A is oxygen or NH, Alk is $C_{1-10}$ alkylene, R' is identical or different alkyl, aryl or aralkyl containing up to 22 carbon atoms, wherein a maximum of 2 R' groups are hydrogen atoms, and $X^{\oplus}$ is said anion.

3. The adhesive of claim 2, wherein A is NH.

4. The adhesive of claim 2, wherein A is O.

5. The adhesive of claim 2, wherein Alk is a $C_{2-8}$ alkylene group.

6. The adhesive of claim 2, wherein $X^{\oplus}$ is an organic carboxylic acid anion having 8-20 carbon atoms.

7. The adhesive of claim 1, wherein said salt form of an amino group-containing monomer is a quaternary ammonium salt.

8. The adhesive of claim 1, wherein said copolymer salt further comprises a copolymerizable comonomer selected from the group consisting of acrylamide, methacrylamide, hydroxyalkyl esters of acrylic acid or methacrylic acid, polyalkylene glycol esters of acrylic acid or methacrylic acid, ethylene, vinyl acetate, vinyl propionate and vinlypyrrolidone in amounts less than 20 wt %.

9. The adhesive of claim 1, wherein said copolymer salt has a molecular weight in a range between about 20,000 and 250,000.

10. The adhesive of claim 1, further comprising 2–200 wt % of a plasticizer.

11. The adhesive of claim 1, comprising about 1–10 wt % water based on the anhydrous copolymer salt.

12. The adhesive of claim 1, wherein 50–100% of said amino group-containing monomer is in said salt form.

13. The adhesive of claim 1, wherein 80–100% of said amino group-containing monomer is in the salt form.

14. An aqueous solution comprising 20–90 wt % water and 10–80 wt % of the adhesive of claim 1.

15. The solution of claim 14, having a viscosity of about 10 mPa.s to 10 Pa.s.

16. A method of adhering an object selected from the group consisting of a bandage, clothing and plaster to skin, comprising interposing the pressure sensitive adhesive of claim 1 between said object and skin and applying pressure to said object.

17. The method of claim 16, wherein said object or said adhesive contains a topical or systemic pharmaceutical ingredient.

18. An object for topical application to skin comprising a substrate, selected from the group consisting of a fabric, film and tape, wherein said substrate is coated on at least one surface thereof with the adhesive of claim 1.

19. The object of claim 18, wherein said substrate is a fabric, film or tape laminate.

20. The object of claim 18, wherein said substrate or adhesive contains a topical or systemic pharmaceutical ingredient.

* * * * *